United States Patent [19]

Oxford et al.

[11] Patent Number: 5,026,722

[45] Date of Patent: Jun. 25, 1991

[54] INDOLE DERIVATIVES

[75] Inventors: Alexander W. Oxford; Peter C. North, both of Royston; David J. Cavalla, Cambridge, all of England

[73] Assignee: Glaxo Group Limited, England

[21] Appl. No.: 366,462

[22] Filed: Jun. 15, 1989

[30] Foreign Application Priority Data

Jun. 16, 1988 [GB] United Kingdom ............... 8814277

[51] Int. Cl.[5] .............. C07D 403/12; C07D 403/14; A61K 31/55; A61K 31/415
[52] U.S. Cl. .................... 514/397; 514/212; 514/323; 540/603; 546/201; 548/336
[58] Field of Search ............. 548/336; 514/397, 212, 514/323; 546/201; 540/603

[56] References Cited

U.S. PATENT DOCUMENTS

| 3,980,668 | 9/1976 | Buchanan et al. |
| 4,619,941 | 10/1986 | Wright, Jr. et al. ............... 548/336 |
| 4,808,581 | 2/1989 | Oxford et al. ............... 548/336 |
| 4,814,344 | 3/1989 | Humber et al. ............... 548/336 |
| 4,826,838 | 5/1989 | Richardson et al. |

FOREIGN PATENT DOCUMENTS

| 0144986 | 6/1985 | European Pat. Off. |
| 393766 | 10/1990 | European Pat. Off. |
| 2152049B | 7/1985 | United Kingdom |
| 2199579A | 7/1988 | United Kingdom |

OTHER PUBLICATIONS

Chem. Abs., 1972, 76(9), 46033k.
Chem. Abs., 1969, 70(21), 96532u.

Primary Examiner—Mary C. Lee
Assistant Examiner—Lenora Miltenberger
Attorney, Agent, or Firm—Bacon & Thomas

[57] ABSTRACT

The invention relates to indole derivatives of the general formula (I)

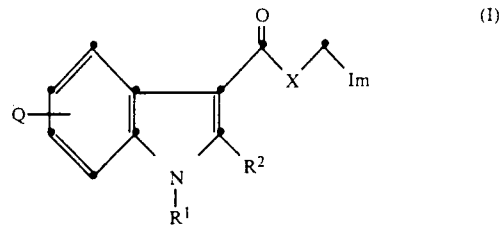

wherein
Im represents an imidazolyl group of the formula:

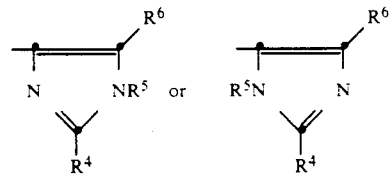

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl or phenyl$C_{1-3}$ alkyl;

$R^2$ represents a hydrogen atom or a group selected from $C_{1-6}$alkyl, $C_{3-6}$alkenyl, $C_{3-7}$cycloalkyl, phenyl or phenyl$C_{1-3}$alkyl;

X represents an oxygen atom or the group $NR^3$ (where $R^3$ represents a hydrogen atom or a $C_{1-6}$alkyl group);

one of the groups represented by $R^4$, $R^5$ and $R^6$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$ alkyl group;

Q represents a hydrogen or a halogen atom, or a hydroxy, $C_{1-4}$alkoxy, phenyl$C_{1-3}$alkoxy or $C_{1-6}$alkyl group or a group $-NR^7R^8$ or $-CONR^7R^8$ (wherein $R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring);

and physiologically acceptable salts and solvates thereof.

The compounds are potent and selective antagonists of the effect of 5-HT at 5-HT$_3$ receptors and are useful, for example, in the treatment of psychotic disorders, anxiety, and nausea and vomiting.

10 Claims, No Drawings

INDOLE DERIVATIVES

This invention relates to indole derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as $5\text{-}HT_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at $5\text{-}HT_3$ receptors have been described previously.

Thus, for example, published European Patent Specification No. 242973 discloses ketone derivatives which may be represented by the general formula (A):

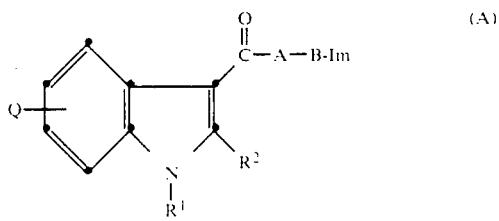

wherein
Im represents an imidazolyl group of formula:

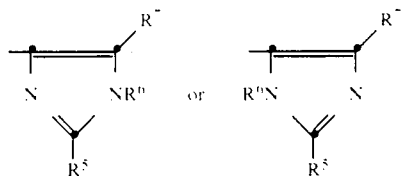

Q represents a hydrogen atom;
$R^1$ represents a hydrogen atom or a $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl or phenyl$C_{1-3}$alkyl group;
$R^2$ represents a hydrogen atom or a $C_{1-6}$alkyl, $C_{3-6}$alkenyl, $C_{3-7}$cycloalkyl, phenyl or phenyl$C_{1-3}$alkyl group;
A—B represents the group $R^3R^4C$—$CH_2$ or $R^3C$=$CH$;
$R^3$ and $R^4$, which may be the same or different, each represents a hydrogen atom or a $C_{1-6}$alkyl group;
one of the groups represented by $R^5, R^6$ and $R^7$, is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group; and physiologically acceptable salts and solvates thereof.

Published European Patent Specification No. 266899 discloses ketone derivatives which may also be represented by the general formula (A), and also possess $5\text{-}HT_3$ antagonist activity, but wherein Im represents an imidazolyl group of formula:

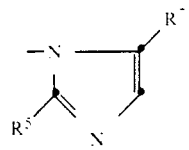

wherein
$R^5$, $R^6$ and $R^7$ are as defined in EPA 242973, although one of these groups may additionally represent a vinyl group;
$R^1$ is as defined in EPA 242973, although one of these group may additionally represent a group selected from —$CO_2R^{10}$, —$COR^{10}$, —$CONR^{10}R^{11}$ or —$SO_2R^{10}$ (wherein $R^{10}$ and $R^{11}$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^{10}$ does not represent a hydrogen atom when $R^1$ represents a group —$CO_2R^{10}$ or —$SO_2R^{10}$);
$R^2$ is as defined in EPA 242973;
A—B represents the group $R^3R^4C$—$CH_2$ wherein $R^3$ and $R^4$ are as defined in EPA 242973;
Q represents a hydrogen atom or a halogen atom or a hydroxy, $C_{1-4}$alkoxy, phenyl$C_{1-3}$alkoxy or $C_{1-6}$alkyl group or a group —$NR^7R^8$ or —$CONR^7R^8$ (wherein $R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring);
and physiologically acceptable salts and solvates thereof.

U.S. Pat. No. 4,619,941 discloses indole carboxamides which may be represented by the general formula (B):

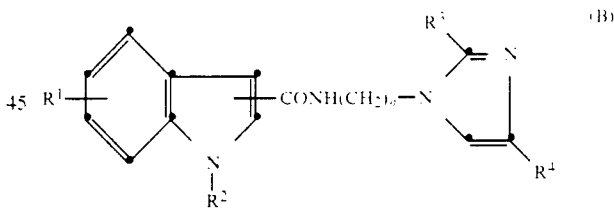

wherein
$R^1$ represents a hydrogen or a halogen atoms, or a $C_{1-3}$alkyl or $C_{1-3}$alkoxy group;
$R^2$ represents a hydrogen atom or a $C_{1-3}$alkyl or benzyl group; n represents an integer from 2 to 8;
and $R^3$ and $R^4$ independently represent a hydrogen atom, or a $C_{1-3}$alkyl or phenyl group;
and acid addition salts thereof.

However, these compounds are described in U.S. Pat. No. 4,619,941 as inhibitors of the enzyme thromboxane synthetase which are useful in the treatment of, for example, ischaemic heart disease.

We have now found a novel group of compound which differ in structure from those described previously, and which are potent antagonists of the effect of 5-HT at $5\text{-}HT_3$ receptors.

Thus the present invention provides an indole derivative of the general formula (I):

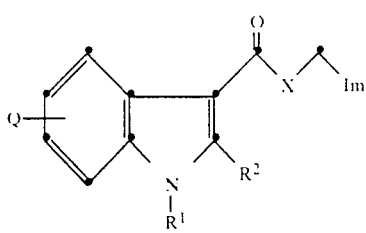

wherein

Im represents an imidazolyl group of the formula:

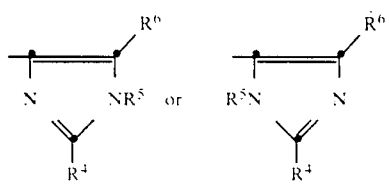

$R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$ alkyl, phenyl or phenyl$C_{1-3}$alkyl;

$R^2$ represents a hydrogen atom or a group selected from $C_{1-6}$alkyl, $C_{3-6}$alkenyl, $C_{3-7}$cycloalkyl, phenyl or phenyl$C_{1-3}$alkyl;

X represents an oxygen atom or the group $NR^3$ (where $R^3$ represents a hydrogen atom or a $C_{1-6}$alkyl group);

one of the groups represented by $R^4$, $R^5$ and $R^6$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

Q represents a hydrogen or a halogen atom, or a hydroxy, $C_{1-4}$alkoxy, phenyl$C_{1-3}$alkoxy or $C_{1-6}$alkyl group or a group $-NR^7R^8$ or $-CONR^7R^8$ (wherein $R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring);

and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

All optical isomers of compounds of general formula (I) and their mixtures including the racemic mixtures thereof, and all the geometric isomers of compounds of formula (I), are embraced by the invention.

Referring to the general formula (I), the alkyl groups represented by $R^1$, $R^2$, $R^3$, $R^4$, $R^5$, $R^6$, $R^7$, $R^8$ and Q may be straight chain or branched chain alkyl groups, for example, methyl, ethyl, propyl, prop-2-yl, butyl, but-2-yl or 2-methylprop-2-yl, and, in the case of $R^1$ to $R^6$ and Q, pentyl, pent-3-yl or hexyl. An alkenyl group may be, for example, a propenyl or butenyl group. An alkynyl group may be, for example, a prop-2-ynyl or oct-2-ynyl group. When $R^1$ or $R^5$ represents a $C_{3-6}$alkenyl group or $R^1$ represents a $C_{3-10}$alkynyl group, or $R^7$ or $R^8$ represents a $C_{3-4}$alkenyl group, the double or triple bond may not be adjacent to the nitrogen atom. A phenyl$C_{1-3}$ alkyl group (as such or as part of a phenyl$C_{1-3}$alkoxy group) may be, for example, a benzyl, phenethyl or 3-phenylpropyl group. A cycloalkyl group (as such or as part of a cycloalkylalkyl group) may be, for example, a cyclopropyl, cyclobutyl, cyclopentyl, cyclohexyl or cycloheptyl group. When Q represents a $C_{1-4}$alkoxy group it may be, for example, a methoxy group. When Q represents a halogen atom it may be, for example, a fluorine, chlorine or bromine atom. The substituent Q may be at the 4, 5, 6 or 7-position of the indole moiety.

A preferred class of compounds of formula (I) is that in which $R^1$ represents a hydrogen atom or a $C_{1-3}$alkyl (e.g. methyl) group.

Another preferred class of compounds of formula (I) is that in which $R^2$ represents a $C_{1-3}$alkyl (e.g. methyl) group, or, more preferably, a hydrogen atom.

A further preferred class of compounds of formula (I) is that in which X represents an oxygen atom or the group $NR^3$, and $R^3$ represents a hydrogen atom or a $C_{1-3}$alkyl (e.g. methyl or isopropyl) group. Most preferably, X represents the group $NR^3$, and $R^3$ represents a $C_{1-3}$alkyl (e.g. methyl) group.

Another preferred class of compounds of formula (I) is that in which $R^4$, $R^5$ and $R^6$ each independently represent a hydrogen atom or a $C_{1-4}$alkyl (e.g. methyl)group. A further preferred class of compounds is that wherein $R^4$ and $R^5$ each represent a hydrogen atom, and $R^6$ is a $C_{1-3}$alkyl (e.g. methyl or n-propyl) group.

A further preferred class of compounds of formula (I) is that in which Q represents a hydrogen or a halogen (e.g. fluorine) atom, more particularly a fluorine atom. Q, when other than a hydrogen atom, is most preferably at the 7-position of the indole moiety.

A preferred group of compounds according to the invention is that in which $R^1$ represents a $C_{1-3}$alkyl group; $R^2$ represents a hydrogen atom; X represents the group $NR^3$ and $R^3$ is a $C_{1-3}$alkyl group; $R^4$ and $R^5$ each represent a hydrogen atom; $R^6$ represents a $C_{1-3}$alkyl group; and Q represents a hydrogen or, more preferably, a fluorine atom.

A particularly preferred compound according to the invention is N,1-dimethyl-7-fluoro-N-[(5-methyl-1H-imidazol-4-yl)methyl]-1H-indole-3-carboxamide and its physiologically acceptable salts and solvates.

A further preferred compound according to the invention is N,1-dimethyl-N-[(5-methyl-1H-imidazol-4-yl)methyl]-1H-indole-3-carboxamide and its physiologically acceptable salts and solvates.

The potent and selective antagonism of 5-HT at 5-HT$_3$ receptors by the compounds of the invention may be demonstrated by their ability to inhibit 3-(5-methyl-1H-imidazol-4-yl)-1-[1-(methyl-t$_3$)-1H-indol-3-yl]-1-propanone binding in rat entorhinal cortex homogenates (following the general procedure described by G. Kilpatrick et al in *Nature*, 1987, 330, 746), and/or by their ability to inhibit the 5-HT-induced depolarisation of the rat isolated vagus nerve preparation.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; pain; dependency on drugs or substances of abuse; depression; or dementia or another cognitive disorder, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxylpropyl methylcellulose); fillers (e.g., lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine or 1-methyl-5-[[3-[3-(1-piperidinylmethyl)phenoxy]propyl]amino]-1H-1,2,4-triazole -3-methanol, cimetidine, famotidine, nizatidine or roxatidine) or $H^+K^+ATPase$ inhibitors (e.g. omeprazole). In the treatment of nausea and vomiting, compounds of formula (I) may also be administered in combination with dexamethasone.

A proposed dose of the compounds of the invention for administration to man (of approximately 70 kg body weight) is 0.001 to 100 mg, preferably 0.01 to 50 mg, of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I), and physiologically acceptable salts or solvates thereof, may be prepared by the general methods outlined hereinafter. In the following description, the groups $R^1$, $R^2$, $R^3$, Q and Im are as previously defined for compounds of general formula (I) unless otherwise stated.

According to a first general process (A), a compound of general formula (I), wherein X represents the group $NR^3$ may be prepared by reacting an acid of formula (II):

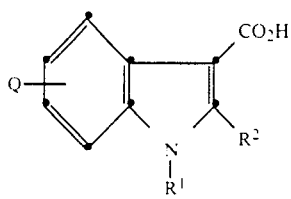
(II)

or an activated derivative thereof, with a compound of formula (III):

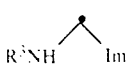
(III)

or a salt or protected derivative thereof, optionally in the presence of a base (e.g. triethylamine or N,N-diisopropylethylamine), followed where necessary by removal of any protecting groups.

Suitable activated derivatives of the acid (II) include acid halides (e.g. acid chlorides), anhydrides (e.g. symmetrical anhydrides or mixed anhydrides) and esters. When an activated derivative of the acid (II) is used the reaction may be conveniently effected in an inert solvent such as an ether (e.g. tetrahydrofuran), a halogenated hydrocarbon (e.g. dichloromethane or 1,2-dichloroethane) or a nitrile (e.g. acetonitrile) and at a temperature of, for example $-10$ to $+100°$ C.

Alternatively, a compound of general formula (I), wherein X represents the group $NR^3$, may be prepared by the reaction of the free acid (II) with the amine (III) using standard coupling reagents for peptide synthesis (e.g. diphenylphosphoryl azide, dicyclohexylcarbodiimide or N,N'-carbonyldiimidazole). The reaction may be conveniently effected in an inert solvent and at a temperature as described above.

Activated derivatives corresponding to the acids of formula (II) may be prepared by conventional methods. Thus an acid halide may be prepared by reacting an acid (II) or a salt thereof with a halogenating reagent (e.g. thionyl chloride).

Anhydrides may be prepared by reacting an acid (II) with an appropriate acid halide in the presence of a base, or alternatively by reacting an acid halide corresponding to the compound of formula (II) with an acid, in the presence of a base.

Esters may be prepared by reacting an acid halide or anhydride corresponding to the compound of formula (II) with an appropriate alcohol, optionally in the presence of a base (e.g. triethylamine or pyridine).

According to another general process (B), a compound of general formula (I), wherein X represents an oxygen atom, may be prepared by reacting a compound of formula (II) or an activated derivative thereof with a compound of formula (IV):

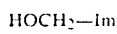 (IV)

or a protected derivative thereof, followed where necessary by removal of any protecting groups.

Suitable activated derivatives of the acid (II) include acid halides (e.g. acid chlorides) and anhydrides (e.g. symmetrical anhydrides or mixed anhydrides).

When an activated derivative of the acid (II) is used, the reaction may be conveniently effected in a solvent such as an ether (e.g. tetrahydrofuran), a halogenated hydrocarbon (e.g. 1,2-dichloroethane) or an amide (e.g. dimethylformamide) and at a temperature of, for example, $-10$ to $+110°$ C. Alternatively, a compound of general formula (I), wherein X represents an oxygen atom, may be prepared by reaction of the free acid (II) with the alcohol (IV), preferably in the presence of an acid catalyst (e.g. sulphuric acid or p-toluenesulphonic acid) or in the presence of a dehydrating agent (e.g. dicyclohexylcarbodiimide or trifluoroacetic acid). The reaction may be conveniently effected in a solvent and at a temperature as described above.

Activated derivatives of the acid of formula (II) may be prepared using conventional methods, for example as described in process (A) above.

According to another general process (C), a compound of general formula (I) may be converted into another compound of formula (I) using conventional techniques. Such conventional techniques include hydrogenation, alkylation and acid-catalysed cleavage using protection and deprotection where necessary.

Thus, according to one embodiment of the interconversion process (C), hydrogenation may be used to convert an alkenyl or an alkynyl substituent into an alkyl substituent, or an alkynyl into an alkenyl substituent, or a benzyloxy substituent into a hydroxyl group. Hydrogenation according to general process (C) may be effected using conventional procedures, for example, using hydrogen in the presence of a catalyst, as described in published European Patent Specification No. 242973.

The term 'alkylation' according to general process (C) includes the introduction of groups such as cycloalkyl, alkenyl or phenalkyl groups.

Thus, for example, a compound of formula (I) in which $R^1$ represents a $C_{1-6}$alkyl, $C_{3-6}$alkenyl, $C_{3-10}$alkynyl, $C_{3-7}$-cycloalkyl, $C_{3-7}$-cycloalkylC$_{1-4}$alkyl, or phenylC$_{1-3}$alkyl group may be prepared by alkylating a compound of formula (I) in which $R^1$ represents a hydrogen atom, or a compound in which $R^5$ represents a $C_{1-6}$alkyl, $C_{3-7}$cycloalkyl, $C_{3-6}$alkenyl or phenylC$_{1-3}$alkyl group may be prepared by alkylating the corresponding compound of formula (I) in which $R^5$ represents a hydrogen atom, using conventional procedures, for example as described in published European Patent Specification No. 242973. Thus the reactions may be effected using an appropriate alkylating agent of formula $R^9Z$ (where $R^9$ is the group to be introduced and Z is a leaving atom or group), preferably in the presence of a base.

According to a yet further embodiment of general process (C), a compound of formula (I) in which Q represents a hydroxyl group may be prepared from the corresponding compound in which Q represents an alkoxy or benzyloxy group by acid-catalysed cleavage. The reaction may be effected using a Lewis acid such as boron tribromide or aluminium trichloride, in a solvent such as a halogenated hydrocarbon (e.g. dichloromethane). The reaction temperature may conveniently be in the range $-80$ to $+100°$ C.

It should be appreciated that in the above transformations it may be necessary or desirable to protect any sensitive groups in the molecule of the compound in question to avoid undesirable side reactions. For example, it may be necessary to protect the indole and/or imidazole nitrogen atoms, for example with an arylmethyl (e.g. trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group. When Q represents a hydroxyl group it may be necessary to protect the hydroxyl group, for example with an arylmethyl (e.g. benzyl or trityl) group.

Thus according to another general process (D), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example, a trityl group may be cleaved by acid hydrolysis (e.g. using dilute hydrochloric or acetic acid). An alkoxyalkyl group may be removed using a mineral acid (e.g. dilute hydrochlorice acid). An acyl group may be removed by hydrolysis under acidic or basic conditions (e.g. using hydrogen bromide or sodium hydroxide). A sulphonyl group may be removed by alkaline hydrolysis. An arylmethyl OH-protecting group may be cleaved under acidic conditions (e.g. with dilute acetic acid, hydrobromic acid or boron tribromide) or by hydrogenolysis in the presence of a catalyst (e.g. palladium on charcoal).

Compounds of formula (III) and protected derivatives thereof are either known, or may be prepared by reacting a compound of formula (V):

    

or a protected derivative thereof with the appropriate amine (R³NH₂) or salt thereof, followed by reduction of the imine so formed with, for example, sodium cyanoborohydride.

Compounds of formula (V) and protected derivatives thereof may be prepared, for example, by the method described in published European Patent Specification No. 242973.

Compounds of formulae (II) and (IV) and protected derivatives thereof, are either known or may be prepared from known compounds by conventional methods.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E.L. Eliel (McGraw Hill, 1962) and 'Tables of Resolving Agents' by S. H. Wilen.

The various general methods described above may be used for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in °C. Thin layer chromatography (t.l.c.) was carried out on silica, and flash column chromatography (FCC) on silica (Merck 9385). Solvent System A as used for chromatography denotes dichloromethane:ethanol:0.88 ammonia solution. Organic extracts were dried, where indicated, over sodium sulphate or magnesium sulphate. The following abbreviation are used: DMF-dimethylformamide, THF-tetrahydrofuran.

Intermediate 1

N,5-Dimethyl-1-(triphenylmethyl)-1H-imidazole-4-methanamine

A mixture of 5-methyl-1-(triphenylmethyl)-1H-imidazole-4-carboxaldehyde (3.2 g) and methylamine hydrochloride (3.6 g) in methanol (60 ml) was stirred at room temperature for 1h. The mixture was then cooled to 0°, treated with sodium cyanoborohydride (0.62 g) for 2h and water (40 ml) was added. The resulting mixture was then stirred at 20° for 0.5h, cooled to 0° and treated with concentrated hydrochloric acid (10 ml). The mixture was then allowed to warm to 20°, and stirred at 20 for a further 1h and basified (to pH9) with potassium carbonate. The alkaline aqueous mixture was diluted with water (100 ml) and extracted with ethyl acetate (×200 ml). The combined organic extracts were dried and evaporated to leave a foam (3.5 g) which was purified by FCC eluting with System A (100:8:1) to give the title compound (1.8 g) as a solid, t.l.c. (System A, 100:3:1) Rf 0.1.

Intermediate 2

5-Methyl-N-(1-methylethyl)-1-(triphenylmethyl)-1H-imidazole-4-methanamine

A mixture of 5-methyl-1-(triphenylmethyl)-1H-imidazole-4-carboxaldehyde (3.5 g) and isopropylamine (10 ml) in methanol (125 ml) was stirred at 20° for 1h. The resulting solution was treated with ethanolic hydrogen chloride (0.027 g/ml; 15 ml), cooled to 0° and treated with sodium cyanoborohydride (0.94 g). After stirring for 2.5 h, water (15 ml) was added and the resulting mixture was stirred at 20° for 0.5 h and treated with concentrated hydrochloric acid (6 ml). The mixture was warmed to 40°, stirred at 40° for 0.5h and concentrated in vacuo to ca. 50 ml. The concentrate was then basified (to pH9) with a saturated solution of potassium carbonate (200 ml) and extracted with ethyl acetate (3×100 ml). The organic extracts were combined, dried and evaporated to leave a gum (ca. 5 g) which was purified by FCC eluting with System A (100:8:1) to give the title compound (1.9 g) as a solid, m.p. 154°–156°. A second crop of product (0.4 g) has m.p. 150°–154°.

Intermediate 3

4-Methylamino-N,N-dimethyl-5-propyl-1H-imidazole-1-sulphonamide hydrochloride 4-(Chloromethyl)-N,N-dimethyl-5-propyl-1H-imidazole-1-sulphonamide (189 mg) was stirred with excess methylamine (33% solution in ethanol; 5 ml) at room temperature under nitrogen for 18 h. The reaction mixture was evaporated under reduced pressure to give the title compound as an oil (167 mg), t.l.c. (System A, 100:10:1) Rf 0.21.

Intermediate 4

7-Fluoroindole-3-carboxaldehyde

Phosphoryl chloride (2.0 ml) was added to DMF (3 ml) under nitrogen at 0° and to this mixture was added 7-fluoroindole (2.1 g) in dry DMF (4 ml). The mixture was stirred for 1h, 5N sodium hydroxide solution (50 ml) was added, and stirring was continued at 50° for 1h. The mixture was then diluted with water (200 ml) and extracted with ethyl acetate (2×200 ml). The combined, dried organic extracts were evaporated in vacuo to give the title compound (2.07 g), m.p. 203°–205°.

Intermediate 5

7-Fluoro-1-methylindole-3-carboxaldehyde

7-Fluoroindole-3-carboxaldehyde (2.5 g) in dry THF (20 ml) was added to a cold (0°) suspension of sodium hydride (73.2% dispersion in oil; 652 mg) in dry THF (20 ml) under nitrogen and the mixture was stirred for 1h. Methyl iodide (2.5 ml) was added, and the resulting mixture was stirred for 2h at 0°. The mixture was then poured into saturated brine solution (300 ml) and extracted with ether (2×300 ml). The combined, dried organic extracts were evaporated in vacuo to give the title compound (2.66 g), m.p. 92°–94°.

Intermediate 6

7-Fluoro-1-methyl-indole-3-carboxylic acid

7-Fluoro-1-methylindole-3-carboxaldehyde (1.0 g) was dissolved in t-butanol (50 ml). 1.25M Sodium hydrogen phosphate (20 ml) was added followed by 1.0M potassium permanganate (30 ml), and the mixture was stirred at 20 for 16h. 2M Hydrochloric acid (200 ml) was then added and the mixture was extracted with ethyl acetate (2×200 ml). The combined, dried organic extracts were evaporated in vacuo to leave a solid which was purified by FCC eluting with hexane:ether (1:1) followed by hexane:ether:acetic acid (50:50:1) to give the title compound (192 mg), m.p. 225°–227°.

EXAMPLE 1

N-[(1H-Imidazol-4-yl)methyl]-1H-indole-3-carboxamide hydrochloride

A suspension of indole-3-carboxylic acid (0.592 g) and thionyl chloride (0.6 ml) in 1,2-dichloroethane (50 ml) was stirred at room temperature for 60h under nitrogen. The suspension was evaporated in vacuo and further 1,2-dichloroethane (50 ml) was added. The suspension was re-evaporated to give a solid (0.6 g) which was dissolved in acetonitrile (25 ml) and triethylamine (5 ml), and added to a stirred suspension of imidazole-4-methanamine dihydrochloride (0.684 g) and triethylamine (5 ml) in acetonitrile (25 ml) at −5° under nitrogen. The reaction was stirred for 1h while warming to room temperature and then heated at reflux for 20h. The mixture was evaporated in vacuo, dissolved in methanol (20 ml) and partitioned between hydrochloric acid (0.2N; 2×200 ml) and dichloromethane (2×100 ml). The combined aqueous layers were basified with saturated potassium carbonate and extracted with chloroform (3×150 ml). The combined chloroform layers were dried and evaporated in vacuo to give a semi-solid which was triturated with ether to give a solid (0.24 g). This was adsorbed onto silica and purified by FCC eluting with System A (83.5:15:1.5) to give a solid (ca. 50 mg) which was dissolved in methanol (3 ml) and acidified with ethanolic hydrogen chloride. Dry ether (20 ml) was added until the solution turned cloudy, precipitating the title compound (26 mg), m.p. 225°–229° (decomp.).

Analysis Found: C,55.1; H,4.7; N,19.5; $C_{13}H_{12}N_4O$ . HCl. $0.38H_2O$ requires C,55.1; H,4.5; N,19.5%

Water Assay Found 2.49% w/w $H_2O \equiv 0.38$ mol $H_2O$.

EXAMPLE 2

N-[(1H-Imidazol-4-yl)methyl]-1-methyl-1H-indole-3-carboxamide maleate

Triethylamine (0.27 ml) was added dropwise to a stirred suspension of 1-methyl-1H-indole-3-carboxylic acid (175 mg) and imidazole-4-methanamine (97 mg) in dry dichloromethane at room temperature under nitrogen. Diphenylphosphoryl azide (0.43 ml) was then added and stirring was continued for 20h. The reaction mixture was partitioned between hydrochloric acid (1N; 150 ml) and ethyl acetate (2×75 ml) and the aqueous layer was carefully basified (to pH9) with solid potassium carbonate and extracted into ethyl acetate (3×75 ml). These latter ethyl acetate extracts were combined, dried and evaporated in vacuo to leave a solid (0.15 g) which was dissolved in absolute ethanol (25 ml), and a solution of maleic acid (95 mg) in ethanol (2 ml) was added with stirring. The resulting solution was diluted with dry ether (ca. 200 ml), precipitating the title compound (110 mg), m.p. 145°–147°.

Analysis. Found: C,57.5; H,4.3; N,14.7; $C_{14}H_{14}N_4O$ . $1.1C_4H_4O_4$. $0.046H_2O$ requires C,57.7; H,4.8; N,14.6%.

Water Assay Found 0.223% w/w $H_2O \equiv 0.046$ mol $H_2O$.

EXAMPLE 3

N,1-Dimethyl-N-[(5-methyl-1H-imidazol-4-yl)methyl]-1H-indole-3-carboxamide d,l-tartrate A mixture of 1-methyl-1H-indole-3-carboxylic acid (0.73 g) and N,5-dimethyl-1-(triphenylmethyl)-1H-imidazole-4-methanamine (1.6 g) in dry THF (100 ml) under nitrogen was treated with triethylamine (1.2 ml) followed by diphenylphosphoryl azide (1.8 ml). The resulting solution was stirred at room temperature for 20h, diluted with water (20 ml) and acetic acid (20 ml) and heated on a steam bath for 1h. The mixture was then cooled to 20°, evaporated in vacuo to ca. 30 ml, diluted with dilute hydrochloric acid (2M; 100 ml) and extracted with ethyl acetate (2×100 ml); extracts discarded). The acidic aqueous layer was basified (to pH8) with potassium carbonate and extracted with ethyl acetate (3×100 ml). The combined organic extracts were dried and evaporated to leave a gum (1.0 g) which was purified by FCC eluting with System A (100:8:1) to give a gum (0.7 g) which was further purified by FCC eluting with System A (150:8:1) to give a gum (0.37 g). This was dissolved in ethanol (10 ml) and treated with a hot solution of d,l-tartaric acid (196 mg) in ethanol (10 ml). The resulting solution was diluted with dry ether (200 ml) to precipitate the title compound (0.41 g) as a solid, t.l.c. (System A, 100:8:1) Rf 0.15.

Analysis. Found: C,54.8; H,5.6; N,12.4; $C_{16}H_{18}N_4O \cdot C_4H_6O_6 \cdot 0.34H_2O$ requires C,54.8; H,5.7; N,12.8%.

Water Assay Found 1.43% w/w $H_2O \equiv 0.34$ mol $H_2O$.

EXAMPLE 4

[(1H-Imidazol-4-yl)methyl]-1-methyl-1H-indole-3-carboxylate maleate

A stirred suspension of 1-methyl-1H-indole-3-carboxylic acid (0.5 g) in dry 1,2-dichloromethane (20 ml) at room temperature was treated with thionyl chloride (0.5 ml) and heated at reflux for 2h. The resulting solution was evaporated in vacuo to give a solid. This was dissolved in dry 1,2-dichloroethane (20 ml), cooled at 0°, stirred, and treated dropwise with a suspension of 1-(triphenylmethyl)-1H-imidazole-4-methanol (1.02 g) in dry 1,2-dichloroethane (15 ml) and dry DMF (10 ml). Stirring was continued for 17h and the resulting solution was poured into a mixture of sodium carbonate (2N;75 ml) and chloroform (100 ml). The organic layer was washed twice with brine (75 ml), dried and evaporated in vacuo to give a semi-solid (1.7 g). This was dissolved in a mixture of acetic acid:water:THF (2:2:1) (25 ml) and heated at reflux for 0.75h. The cooled solution was partitioned between dichloromethane (100 ml) and hydrochloric acid (1N; 100 ml). The acidic layer was further washed with chloroform (50 ml), basified with saturated potassium carbonate (pH8) and extracted with dichloromethane (3×75 ml). These latter dichloromethane extracts were combined, dried and evaporated in vacuo to leave an oil (0.25 g). This oil was dissolved in ethanol (10 ml), and a solution of maleic acid (162 mg) in ethanol (2 ml) was added with stirring, precipitating the title compound (0.35 g), m.p. 148°–150°.

Analysis Found: C,58.1; H,4.6; N,10.7; $C_{14}H_{13}N_3O_2 \cdot C_4H_4O_4 \cdot 0.15EtOAc$ requires C,58.4; H,4.8; N,11.0%.

N.m.r. indicated 0.15 mol of ethyl acetate present.

EXAMPLE 5

1-Methyl-N-(1-methylethyl)-N-[(5-methyl-1H-imidazol-4-yl)methyl]-1H-indole-3-carboxamide d,l-tartrate A solution of 1-methyl-1H-indole-3-carbonyl chloride (0.73 g) in dry dichloromethane (13 ml) was added to a stirred solution of 5-methyl-N-(1-methylethyl)-1-(triphenylmethyl)-1H-imidazole-4-methanamine (1.0 g) in dry dichloromethane (25 ml). The mixture was stirred at 20° for 2h, concentrated in vacuo to leave a gum which was diluted with acetic acid (20 ml), THF (10 ml) and water (20 ml) and heated on a steam bath for 1h. The mixture was cooled, concentrated in vacuo and the residue was partitioned between ethyl acetate (3×90 ml) and saturated potassium carbonate solution (90 ml). The combined organic extracts were dried and evaporated to leave a gum (ca. 2 g) which was purified by FCC eluting with System A (200:8:1) to give a foam (0.75 g). This was dissolved in methanol (30 ml), treated with a methanolic solution (30 ml) of d,l-tartaric acid (360 mg) and the resulting solution was diluted with ethyl acetate (100 ml) and concentrated in vacuo to ca. 25 ml to precipitate the title compound (1.1 g) as a solid, m.p. 173°–175°.

Analysis Found: C,57.4; H,6.0; N,11.9; $C_{18}H_{22}N_4O \cdot C_4H_6O_6$ requires C,57.4; H,6.1; N,12.2%.

EXAMPLE 6

N,1-Dimethyl-N-[(5-propyl-1H-imidazol-4-yl)methyl]-1H-indole-3-carboxamide d, l-tartrate 4-Methylamino-N,N-dimethyl-5-propyl-1Himidazole-1-sulphonamide hydrochloride (233 mg) was suspended in dry dichloromethane (20 ml) at room temperature and N,N-diisopropylethylamine (406 mg) was added, followed by 1-methyl-1H-indole-3-carbonyl chloride (228 mg) in dry dichloromethane (5 ml). The reaction mixture was stirred at room temperature under nitrogen for 24h. The solvent was removed by evaporation under reduced pressure and the residue was dissolved in dimethoxyethane (20 ml). 2N hydrochloric acid (4 ml) was added to this solution and the mixture was heated at reflux for 24h. After cooling, the mixture was poured into 2N sodium carbonate solution (100 ml) and extracted with dichloromethane:ethanol (10:1) (3×100 ml). The combined, dried organic extracts were evaporated under reduced pressure to give an oil (0.30 g) which was purified by FCC eluting with System A (100:15:2) to give the free base of the title compound as an oil (52 mg). The free base was dissolved in ethanol (10 ml) and treated with a solution of di-p-toluoyl-L-tartaric acid (68.5 mg) in ethanol (5 ml). Ether (ca. 5 ml) was added, and the solution was cooled in ice to precipitate a solid. Further purification was effected by liberating the free base from the di-p-toluoyl-tartrate salt by dissolving the salt in dichloromethane (30 ml) and washing the resultant solution with 2N sodium carbonate solution (2×50 ml). The organic layer was then dried and the solvent removed by evaporation under reduced pressure to give the free base as an oil (33 mg). This was dissolved in absolute ethanol (10 ml) and treated with a solution of D,L-tartaric acid (17 mg) in absolute ethanol (5 ml). Ether (ca. 5 ml) was added, and the solution was cooled in ice to precipitate the title compound as a semi-solid, m.p. 90°–92°, t.l.c. (System A, 100:15:2) Rf 0.49.

EXAMPLE 7

N,1-Dimethyl-7-fluoro-N-[(5-methyl-1H-imidazol-4-yl)methyl]-1H-indole-3-carboxamide maleate 7-Fluoro-1-methylindole-3-carboxylic acid (140 mg) was suspended in dry dichloromethane (5 ml) under nitrogen. Oxalyl chloride (0.12 ml) was added, the mixture was stirred for 1h, and the solvent was removed in vacuo. The residue was redissolved in dichloromethane (3 ml), and to this solution was added N,5-dimethyl-1-triphenylmethyl-1H-imidazole-4-methanamine (291 mg) in dry dichloromethane (3 ml), and the resulting mixture was stirred at room temperature for 8h. The solvent was removed in vacuo, acetic acid (4 ml) and water (1 ml) were added, and the mixture was heated at reflux for 2h. The solvent was removed in vacuo and the residue was purified by FCC eluting with System A (100:8:1) to give the free base of the title compound (180 mg). A further portion of the free base (57 mg) was prepared in a similar manner, and the combined material (237 mg) was dissolved in ethanol (6 ml). Maleic acid (92 mg) in ethanol (4 ml) was added and the solvent was removed in vacuo to leave a gum. Trituration with ethyl acetate: ether (2:1) gave the title compound (295.5 mg), m.p. 134°–135°.

Analysis Found: C,57.8; H,5.0; N,13.2; $C_{20}H_{21}FN_4O_5$ requires C,57.7; H,5.1; N,13.45%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

| Direct Compression Tablet | |
|---|---|
| | mg/tablet |
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

INJECTION FOR INTRAVENOUS ADMINISTRATION

| | mg/ml | |
|---|---|---|
| Active ingredient | 0.05 | 1.0 |
| Sodium Chloride BP | as required | as required |
| Water For Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:

1. A compound of the formula (I)

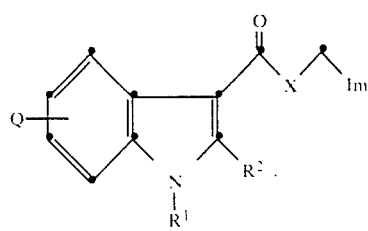

wherein

Im represents an imidazolyl group of the formula:

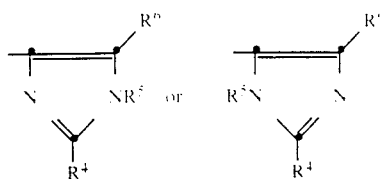

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkylC$_{1-4}$alkyl, phenyl or phenylC$_{1-3}$alkyl;

$R^2$ represents a hydrogen atom or a group selected from $C_{1-6}$alkyl, $C_{3-6}$alkenyl, $C_{3-7}$cycloalkyl, phenyl or phenylC$_{1-3}$alkyl;

X represents an oxygen atom or the group $NR^3$ (where $R^3$ represents a hydrogen atom or a $C_{1-6}$alkyl group);

one of the groups represented by $R^4$, $R^5$ and $R^6$ is a hydrogen atom or a $C_{1-6}$alkyl, $C_{3-7}$cycloalkyl, $C_{3-6}$alkenyl, phenyl or phenylC$_{1-3}$alkyl group, and each of the other two groups, which may be the same or different, represents a hydrogen atom or a $C_{1-6}$ alkyl group;

Q represents a hydrogen or a halogen atom, or a hydroxy, $C_{1-4}$alkoxy, phenylC$_{1-3}$alkoxy or $C_{1-6}$alkyl group or a group $-NR^7R^8$ or $-CONR^7R^8$ (wherein $R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring);

or a physiologically acceptable salt or solvate thereof.

2. A compound according to claim 1 in which $R^1$ represents a hydrogen atom or a $C_{1-3}$alkyl group.

3. A compound according to claim 1 in which $R^2$ represents a hydrogen atom or a $C_{1-3}$alkyl group.

4. A compound according to claim 1 in which X represents the group $NR^3$, and $R^3$ represents a $C_{1-3}$alkyl group.

5. A compound according to claim 1 in which $R^4$ and $R^5$ each represent a hydrogen atom, and $R^6$ represents a $C_{1-3}$alkyl group.

6. A compound according to claim 1 in which Q represents a hydrogen or a halogen atom.

7. A compound according to claim 1 in which $R^1$ represents a $C_{1-3}$alkyl group; $R^2$ represents a hydrogen atom; X represents the group $NR^3$ and $R^3$ is a $C_{1-3}$alkyl group; $R^4$ and $R^5$ each represent a hydrogen atom; $R^6$ represents a $C_{1-3}$alkyl group; and Q represents a hydrogen or a fluorine atom.

8. N,1-Dimethyl-7-fluoro-N-[5-methyl-1H-imidazol-4-yl)methyl]-1-H-indole-3 -carboxamide; N,1-dimethyl-N-[(5-methyl-1H-imidazol-4-yl)methyl]-1H-indole-3-carboxamide or a physiologically acceptable salt or solvate thereof.

9. A pharmaceutical composition for treating a condition mediated through 5-HT$_3$ receptors which comprises an effective amount to relieve said condition of at least one compound of formula (I) as defined in claim 1 or a physiologically acceptable salt or solvate thereof together with at least one physiologically acceptable carrier or excipient.

10. A method of treating a condition mediated through 5-HT$_3$ receptors which comprises administering to a patient an effective amount to relieve said condition of a compound of formula (I) as defined in claim 1 or a physiologically acceptable salt or solvate thereof.

* * * * *